United States Patent [19]

Krause et al.

[11] Patent Number: 4,639,328

[45] Date of Patent: Jan. 27, 1987

[54] THIENOTHIOPHENE DERIVATIVES

[75] Inventors: Joachim Krause, Dieburg; Michael Römer, Rodgau; Georg Weber, Erzhausen, all of Fed. Rep. of Germany

[73] Assignee: Merck Patent Gesellschaft mit beschrankter Haftung, Darmstadt, Fed. Rep. of Germany

[21] Appl. No.: 674,891

[22] Filed: Nov. 26, 1984

[30] Foreign Application Priority Data

Nov. 25, 1983 [DE] Fed. Rep. of Germany ....... 3342631

[51] Int. Cl.[4] .......................... C09K 3/34; G02F 1/13; C07D 409/00
[52] U.S. Cl. .................. 252/299.61; 252/299.5; 350/350 R; 350/350 S; 549/50; 549/20; 549/21; 549/22; 544/238; 544/315; 544/316; 544/318; 544/333; 546/197
[58] Field of Search ............... 549/50; 252/299.61, 252/299.5; 350/350 R, 350 S

[56] References Cited

U.S. PATENT DOCUMENTS

| | | | |
|---|---|---|---|
| 3,189,618 | 6/1965 | Brasen | 549/50 |
| 4,124,596 | 11/1978 | Fadre et al. | 549/50 |
| 4,510,069 | 4/1985 | Eidenschine et al. | 252/299.61 |

FOREIGN PATENT DOCUMENTS

| | | | |
|---|---|---|---|
| 55-151077 | 11/1980 | Japan | 252/299.61 |
| 157980 | 7/1962 | U.S.S.R. | 549/50 |

OTHER PUBLICATIONS

Karamysheva, L. A., et al., Mol. Cryst. Liq. Cryst., vol. 67, pp. 241-252 (1981).
Pavluchenko, A. I., et al., Advances in Liquid Crystal Research & Applications, Bata, L., Ed., Pergamon Press, Oxford, pp. 1007-1013 (1980).
Behringer, H., et al., Liebigs Annalen Chemie, vol. 10, pp. 1729-1750 (1981).
Nash, J. A., et al., Mol. Cryst. Liq. Cryst., vol. 25, pp. 299-321 (1974).
Osman, M. A., et al., Mol. Cryst. Liq. Cryst., vol. 82 (Letters), pp. 339-344 (Jan. 1983).

Primary Examiner—Teddy S. Gron
Attorney, Agent, or Firm—Millen & White

[57] ABSTRACT

Thienothiophene derivatives of the formula I

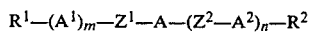

$$R^1-(A^1)_m-Z^1-A-(Z^2-A^2)_n-R^2 \qquad I$$

in which $R^1$ and $R^2$ are each H or an alkyl group having 1-12 C atoms, in which, furthermore, one or two non-adjacent $CH_2$ groups can be replaced by O atoms, —CO— or —CH=CH— groups, or are each F, Cl, Br, CN, —COOR or —O—COR, $A^1$ and $A^2$ are each 1,4-phenylene, 1,4-cyclohexylene, 1,3-dioxane-2,5-diyl, 1,3-dithiane-2,5-diyl, tetrahydropyran-2,5-diyl, pyridazine-3,6-diyl or the corresponding N-oxide, piperidine-1,4-diyl, 1,4-bicyclo[2.2.2]octylene or pyrimidine-2,5-diyl groups which are unsubstituted or substituted by one or two F, Cl or Br atoms and/or CN groups and/or $CH_3$ groups, A is a group of the formula 1 or 2

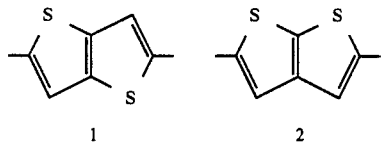

which is unsubstituted or substituted by one or two Cl and/or Br atoms, $Z^1$ and $Z^2$ are each —CO—O—, —O—CO—, —$CH_2CH_2$—, —$OCH_2$—, —$CH_2O$— or a single bond, R is an alkyl group having 1-10 C atoms, m is 1 or 2 and n is 0 or 1, and where m is 2, the two groups $A^1$ can be identical or different, can be used as components of liquid crystalline phases.

18 Claims, No Drawings

THIENOTHIOPHENE DERIVATIVES

This invention relates to new thienothiophenes.

SUMMARY OF THE INVENTION

It is an object of this invention to provide new compounds having valuable properties, e.g., liquid crystalline compounds.

It is another object of this invention to provide novel stable liquid crystalline or mesogenic compounds which are suitable as components of liquid crystalline phases.

Upon further study of the specification and appended claims, further objects and advantages of this invention will become apparent to those skilled in the art.

These objects have been achieved by providing novel thienothiophene derivatives of the formula I

     I in which $R^1$ and $R^2$ are each H or an alkyl group having 1-12 C atoms, in which, furthermore, one or two non-adjacent $CH_2$ groups can be replaced by O atoms, —CO— or —CH=CH— groups, in the latter case, the resultant $R^1$ and $R^2$ groups having 2-12 C— and oxa atoms in total, or are each F, Cl, Br, CN, —COOR or —O—COR; $A^1$ and $A^2$ are each 1,4-phenylene, 1,4-cyclohexylene, 1,3-dioxane-2,5-diyl, 1,3-dithiane-2,5-diyl, tetrahydropyran-2,5-diyl, pyridazine-3,6-diyl or the corresponding N-oxide, piperidine-1,4-diyl, 1,4-bicyclo[2.2.2]octylene or pyrimidine-2,5-diyl groups which are unsubstituted or substituted by one or two F, Cl or Br atoms and/or CN groups and/or $CH_3$ groups; A is a group of the formula 1 or 2

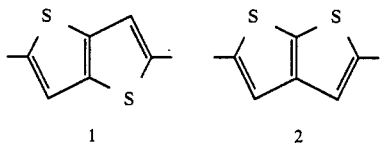

which is unsubstituted or substituted by one or two Cl and/or Br atoms; $Z^1$ and $Z^2$ are each —CO—O—, —O—CO—, —$CH_2CH_2$—, —$OCH_2$—, —$CH_2O$— or a single bond; R is an alkyl group having 1-10 C atoms; m is 1 or 2; and n is 0 or 1; and where m is 2, the two groups $A^1$ can be identical or different.

For the sake of simplicity, in the text which follows Phe is a 1,4-phenylene group, Cy is a 1,4-cyclohexylene group, Dio is a 1,3-dioxane-2,5-diyl group, Bi is a bicyclo[2.2.2.]octylene group, Pip is a piperidine-1,4-diyl group and Pyr is a pyrimidine-2,5-diyl group, and these groups, in particular the 1,4-phenylene group and/or the 1,4-cyclohexylene group, can be unsubstituted or substituted by one or two F and/or Cl and/or Br atoms and/or CN groups and/or $CH_3$ groups.

The compounds of the formula I can be used, like similar compounds, as components of liquid crystalline dielectrics, in particular for displays which are based on the principle of the twisted cell, the guest-host effect, the effect of deformation of aligned phases or the dynamic scattering effect.

It has been found that the compounds of the formula I are outstandingly suitable as components of liquid crystalline phases. They can be used, in particular, for preparing stable liquid craline phases having positive or negative dielectric anisotropy, broad nematic ranges, favorable elastic properties and comparatively low viscosity.

Very generally, the provision of the compounds of the formula I furthermore substantially broadens the range of liquid crystalline substances which are suitable for the preparation of nematic mixtures, from various points of view with regard to application technology.

DETAILED DISCUSSION

The compounds of the formula I have a wide range of use. Depending on the choice of substituents, these compounds can be used as basic materials which form the predominant component of liquid crystalline phases; however, it is also possible for basic liquid crystalline materials obtained from other classes of compounds to be added to the compounds of the formula I, for example in order to vary the dielectric and/or optical anisotropy of such a phase. The compounds of the formula I are furthermore suitable intermediates for the preparation of other substances which can be used as components of a liquid crystalline phase.

The compounds of the formula I in the pure state are colorless and form liquid crystalline meso phases in a temperature range which is advantageous for electro-optical use. They are very stable chemically, thermally and to light.

The invention therefore also relates to the compounds of the formula I and to a process for their preparation, characterized in that a compound which contains one or more reducible groups and/or C—C bonds in place of H atoms, but otherwise corresponds to the formula I, is treated with a reducing agent, or, for the preparation of esters of the formula I (in which $R^1$ and/or $R^2$ are —O—COR or —COOR, and/or in which $Z^1$ and/or $Z^2$ are —CO—O— or —O—CO—), an appropriate carboxylic acid, or one of its reactive derivatives, is reacted with an appropriate alcohol or with one of its reactive derivatives, or, for the preparation of dioxane derivatives of the formula I (in which $A^1$ and/or $A^2$ are 1,3-dioxane-2,5-diyl), an appropriate aldehyde is reacted with an appropriate diol, or, for the preparation of nitriles of the formula I (in which $R^1$ and/or $R^2$ are CN), an appropriate carboxamide is dehydrated or an appropriate carboxylic acid halide is reacted with sulfamide, or a thiophene derivative of the formula II

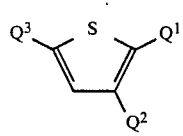     II in which one of the radicals $Q^1$ and $Q^2$ is —CHO, and the other is —$SCH_2$—$Q^3$, and $Q^3$ is $R^1$—$(A^1)_m$—$Z^1$— or $R^2$—$(A^2$—$Z^2)_n$—, is condensed, or, for the preparation of ethers of the formula I (in which $R^1$ and $R^2$ are each alkyl groups, or $R^1$ or $R^2$ is an alkyl group, in which one or two $CH_2$ groups are replaced by O atoms, and/or $Z^1$ and $Z^2$ are each —$OCH_2$— or —$CH_2O$— groups or $Z^1$ or $Z^2$ is a —$OCH_2$— or —$CH_2O$— group), an appropriate hydroxy compound is etherified, and/or, if desired, a chlorine or bromine compound of the formula I (in which $R^1$ and/or $R^2$ are Cl or Br) is reacted with a cyanide.

The invention furthermore relates to the use of the compounds of the formula I as components of liquid crystalline phases.

The invention furthermore relates to liquid crystalline phases which contain at least one compound of the formula I, and liquid crystal display elements, in particular electro-optical display elements, which contain phases of this type.

Above and below, $R^1$, $R^2$, R, A, $A^1$, $A^2$, $Z^1$, $Z^2$, m, n, $Q^1$, $Q^2$ and $Q^3$ are as defined, unless expressly stated otherwise.

The compounds of the formula I accordingly comprise compounds of the part formulae Ia (with two rings), Ib and Ic (each with three rings) and Id (with four rings):

$R^1$—$A^1$—$Z^1$—A—$R^2$  Ia $R^1$—$A^1$—$Z^1$—A—$Z^2$—$A^2$—$R^2$  Ib $R^1$—$(A^1)_2$—$Z^1$—A—$R^2$  Ic $R^1$—$(A^1)_2$—$Z^1$—A—$Z^2$—$A^2$—$R^2$  Id.

The preferred compounds of the part formula Ia comprise those of the part formulae Ie to Ij:

$R^1$—Phe—$Z^1$—A—$R^2$  Ie $R^1$—Cy—$Z^1$—A—$R^2$  If $R^1$—Dio—$Z^1$—A—$R^2$  Ig $R^1$—Pip—$Z^1$—A—$R^2$  Ih $R^1$—Bic—$Z^1$—A—$R^2$  Ii $R^1$—Pyr—$Z^1$—A—$R^2$  Ij

Particularly preferred compounds among these are those of the formulae Ie, If and Ig.

Among the compounds of the part formulae Ib, Ic and Id, those of the part formulae Ik to Iz are particularly preferred:

$R^1$—Phe—$Z^1$—A—$Z^2$—Phe—$R^2$  Ik $R^1$—Dio—$Z^1$—A—$Z^2$—Cy—$R^2$  Il $R^1$—Cy—$Z^1$—A—$Z^2$—Phe—$R^2$  Im $R^1$—Cy—$Z^1$—A—$Z^2$—Cy—$R^2$  In $R^1$—Phe—Phe—$Z^1$—A—$R^2$  Io $R^1$—Phe—Cy—$Z^1$—A—$R^2$  Ip $R^1$—Cy—Phe—$Z^1$—A—$R^2$  Iq $R^1$—Cy—Cy—$Z^1$—A—$R^2$  Ir $R^1$—Phe—Phe—$Z^1$—A—$Z^2$—Phe—$R^2$  Is $R^1$—Phe—Phe—$Z^1$—A—$Z^2$—Cy—$R^2$  It $R^1$—Phe—Cy—$Z^1$—A—$Z^2$—Phe—$R^2$  Iu $R^1$—Phe—Cy—$Z^1$—A—$Z^2$—Cy—$R^2$  Iv $R^1$—Cy—Phe—$Z^1$—A—$Z^2$—Phe—$R^2$  Iw $R^1$—Cy—Phe—$Z^1$—A—$Z^2$—Cy—$R^2$  Ix $R^1$—Cy—Cy—$Z^1$—A—$Z^2$—Phe—$R^2$  Iy $R^1$—Cy—Cy—$Z^1$—A—$Z^2$—Cy—$R^2$  Iz

In the compounds of the formulae above and below, $R^1$ and $R^2$, which can be identical or different, are preferably alkyl, alkoxy (particularly when this radical is on a Phe group) or another oxaalkyl group.

Other preferred compounds of the formula I are those in which one of the radicals $R^1$ and $R^2$ is H, halogen, in particular F, or CN.

$A^1$ and $A^2$ are preferably Cy, Phe or Pyr, or furthermore preferably Dio or Pip; preferably, the compound of the formula I contains no more than one of the radicals Dio, Pip, Bic and Pyr.

Other preferred compounds of the formula I are those which contain at least one cycloaliphatic ring (Cy, Dio, Bi or Pip).

A is preferably an unsubstituted group of the formula 1 or 2.

$Z^1$ and $Z^2$, which can be identical or different, are preferably single bonds, —CO—O—, —O—CO— or —$CH_2CH_2$— groups or, as a second preference, —CO—O— or —O—CO— groups. Particularly preferred are compounds according to the invention wherein one of the groups $Z^1$ and $Z^2$ is a single bond and the other is a —O—CO—, —CO—O— or —$CH_2CH_2$— group.

m is preferably 1 or 2, in particular 1, and n is preferably 0.

Alkyl radicals $R^1$ and/or $R^2$, in which furthermore an ("alkoxy" or "oxaalkyl") or two ("alkoxyalkoxy" or "dioxaalkyl") non-adjacent $CH_2$ groups can be replaced by O atoms, can be straight-chain or branched. They are preferably straight-chain and have 2, 3, 4, 5, 6 or 7 C atoms, and accordingly are preferably ethyl, propyl, butyl, pentyl, hexyl, heptyl, ethoxy, propoxy, butoxy, pentyloxy, hexyloxy, heptyloxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, or methyl, octyl, nonyl, decyl, undecyl, dodecyl, methoxy; octyloxy, nonyloxy, decyloxy, undecyloxy, dodecyloxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

Other preferred compounds of the formula I are those in which $R^2$ is an alkyl radical or an alkoxy radical having 3 to 7 C atoms. Furthermore preferred compounds of the formula I are those, wherein one of the radicals $R^1$ and $R^2$ is a straight chain alkyl group having 2 to 7 C atoms and the other is a straight-chain alkoxy group having 2 to 12 C atoms.

Compounds of the formulae I and Ia to Iz which have branched wing groups $R^1$ or $R^2$ can sometimes be important because of higher solubility in the conventional liquid crystalline base materials, but are particularly important as chiral dopants if they possess optical activity. Branched groups of this type as a rule contain no more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy, 1-methylheptyloxy, 2-oxa-3-methylbutyl and 3-oxa-4-methylpentyl.

In the radicals R, the alkyl groups or alkoxy groups are likewise preferably straight-chain and are, in particular, methyl, ethyl, propyl, butyl or pentyl, in particular methyl, propyl or pentyl.

Preferred compounds of the formulae I and Ia to Iz are those in which at least one of the radicals present has one of the preferred meanings given. Particularly preferred relatively small groups of compounds are those of the formulae Iaa to Iat:

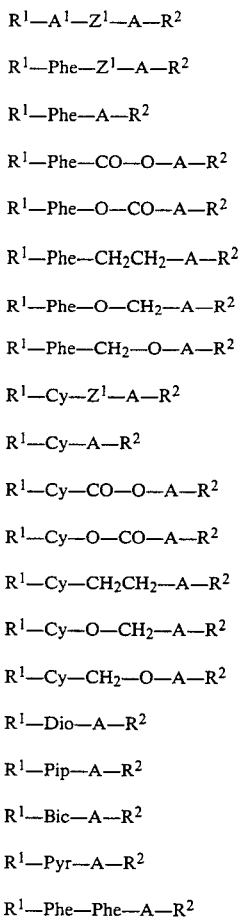

| | |
|---|---|
| $R^1$—$A^1$—$Z^1$—A—$R^2$ | Iaa |
| $R^1$—Phe—$Z^1$—A—$R^2$ | Iab |
| $R^1$—Phe—A—$R^2$ | Iac |
| $R^1$—Phe—CO—O—A—$R^2$ | Iad |
| $R^1$—Phe—O—CO—A—$R^2$ | Iae |
| $R^1$—Phe—$CH_2CH_2$—A—$R^2$ | Iaf |
| $R^1$—Phe—O—$CH_2$—A—$R^2$ | Iag |
| $R^1$—Phe—$CH_2$—O—A—$R^2$ | Iah |
| $R^1$—Cy—$Z^1$—A—$R^2$ | Iai |
| $R^1$—Cy—A—$R^2$ | Iaj |
| $R^1$—Cy—CO—O—A—$R^2$ | Iak |
| $R^1$—Cy—O—CO—A—$R^2$ | Ial |
| $R^1$—Cy—$CH_2CH_2$—A—$R^2$ | Iam |
| $R^1$—Cy—O—$CH_2$—A—$R^2$ | Ian |
| $R^1$—Cy—$CH_2$—O—A—$R^2$ | Iao |
| $R^1$—Dio—A—$R^2$ | Iap |
| $R^1$—Pip—A—$R^2$ | Iaq |
| $R^1$—Bic—A—$R^2$ | Iar |
| $R^1$—Pyr—A—$R^2$ | Ias |
| $R^1$—Phe—Phe—A—$R^2$ | Iat |

Preferred compounds of the formula I which contain a 1,4-cyclohexylene, 1,3-dioxane-2,5-diyl, 1,3-dithiane-2,5-diyl, tetrahydropyran-2,5-diyl and/or piperidine-1,4-diyl-group are those in which these groups are trans-substituted.

Those compounds of the abovementioned formulae which contain one or more of the groups Dio, Pip and/or Pyr include in each case the two possible 2,5- and 1,4-positional isomers. Thus, for example, the part formula Iap embraces the 2-$R^1$-5-(A-$R^2$)-1,3-dioxanes and the 2-(A-$R^2$)-5-$R^1$-1,3-dioxanes, while the part formula Iaq embraces the 1-$R^1$-4-(A-$R^2$)-piperidines and the 1-(A-$R^2$)-4-$R^1$-piperidines.

Where compounds of the formula I have branched wing groups $R^1$ and/or $R^2$, formula I embraces the racemates as well as the optical antipodes and mixtures of these.

The foregoing discussion was directed in large part to the preferred rings Phe, Cy, Dio, Pip, Bi and Pyr but applies fully analogously to the other ring embodiments of $A^1$ and $A^2$. Similarly, it applies fully analogously to the substituted versions of the A, $A^1$ and/or $A^2$ rings. It also applies fully analogously to the alkyl $R^1$ and/or $R^2$ groups containing —CO— and/or —CH=CH— groups.

The compounds of the formula I are prepared by methods which are known per se, as are described in the literature (for example in the standard works, such as Houben-Weyl, Methoden der Organischen Chemie (Methods of Organic Chemistry), Georg-Thieme-Verlag, Stuttgart), the reaction conditions used being those which are conventionally used and suitable for the stated reactions. In this context, it is also possible to use variants which are known per se but have not been specifically stated here.

In the synthesis of the starting materials, in principle all methods can be used which, on the one hand, are conventionally used for the compounds of the formula I which carry other groups in place of the group A and, on the other hand, are conventionally used for the thiophene derivatives of the formula II which carry other radicals in place of the radicals $Q^1$, $Q^2$ and/or $Q^3$. The skilled worker can derive the required synthesis variants by routine methods.

The starting materials can, if desired, also be formed in situ in a procedure in which they are not isolated from the reaction mixture but are immediately reacted further to give compounds of the formula I.

For example, the compounds of the formula I can be prepared by reducing a compound which contains one or more reducible groups and/or C—C bonds in place of H atoms, but otherwise corresponds to the formula I.

Preferred reducible groups are carbonyl groups, in particular keto groups, and furthermore, for example, free or esterified hydroxyl groups or aromatically bonded halogen atoms. Preferred starting materials for the reduction are of the formula I but can contain a cyclohexene ring or cyclohexanone ring in place of a cyclohexane ring, and/or a —CH=CH— group instead of a —$CH_2CH_2$— group, and/or a —CO— group in place of a —$CH_2$— group, and/or an OH group which is free or has been functionally modified (for example in the form of its p-toluenesulfonate) in place of an H atom.

The reduction can be carried out by, for example, hydrogenation of appropriate sulfonates or halides with zinc and an acid (for example glacial acetic acid or hydrochloric acid), or with complex hydrides (for example with $NaBH_4$, advantageously in a solvent, such as dimethyl sulfoxide, or with $LiAlH_4$, advantageously in a solvent, such as diethyl ether, dioxane or tetrahydrofuran). The reduction is preferably carried out at temperatures between about 0° C. and about 100°.

The sulfonates or halides are obtainable by methods known from the literature, for example from the corresponding alcohols, which in turn are obtainable by reduction of the corresponding ketones. Compounds having reducible C—C bonds can be converted to dihalides by methods known from the literature, and the dihalides can then be dehalogenated by the stated methods.

Ketones can furthermore be reduced to the corresponding compounds of the formula I which contain alkyl groups and/or —$CH_2CH_2$-bridges by the methods due to Clemmensen (with zinc, amalgamated zinc or tin and hydrochloric acid, advantageously in aqueous alcoholic solution or in the heterogeneous phase with water/toluene at temperatures between about 80° and 120°) or Wolff-Kishner (with hydrazine, advantageously in the presence of an alkali, such as KOH or NaOH, in a high-boiling solvent, such as diethylene glycol or triethylene glycol, at temperatures between about 100° and 200°).

Esters of the formula I ($R^1$ and/or $R^2$=—O—COR or $Z^1$ and/or $Z^2$=—CO—O— or —O—CO—) can furthermore be obtained by esterification of the corresponding carboxylic acids of the formulae R—COOH, $R^1$—$(A^1)_m$—COOH, $R^1$—$(A^1)_m$—$Z^1$—A—COOH, $R^2$—$(A^2)_n$—COOH or $R^2$—$(A^2$—$Z^2)_n$—A—COOH (or their reactive derivatives) with alcohols or phenols of the formulae $R^1$—$(A^1)_m$—$Z^1$—A—$(Z^2$—$A^2)_n$—OH, $R^2$—$(A^2$—$Z^2)_n$—A—$Z^1$—$(A^1)_m$—OH, $R^2$—$(A^2$—$Z^2)_n$—A—OH, $R^2$—$(A^2)_n$—OH, $R^1$—$(A^1)_m$—$Z^1$—A—OH or $R^1$—$(A^1)_m$—OH (or their reactive derivatives).

Particularly suitable reactive derivatives of the stated carboxylic acids are the acid halides, especially the chlorides and bromides, and furthermore the anhydrides, including, for example, mixed anhydrides of the formulae $R^1$—$(A^1)_m$—CO—O—$COCH_3$, $R^1$—$(A^1)_m$—$Z^1$—A—CO—O—$COCH_3$, $R^2$—$(A^2)_n$—CO—O—$COCH_3$ and $R^2$—$(A^2$—$Z^2)_n$—A—CO—O—$COCH_3$, azides or esters, in particular alkyl esters having 1-4 C atoms in the alkyl group.

Particularly suitable reactive derivatives of the stated alcohols or phenols are the corresponding metal alcoholates or phenolates of the formulae $R^1$—$(A^1)_m$—$Z^1$—A—$(Z^2$—$A^2)_n$—OM, $R^2$—$(A^2$—$Z^2)_n$—A—$Z^1$—$(A^1)_m$—OM, $R^2$—$(A^2$—$Z^2)_n$—A—OM, $R^2$—$(A^2)_n$—OM, $R^1$—$(A^1)_m$—Z1—A—OM and $R^1$—$(A^1)_m$—OM, in which M is one equivalent of a metal, preferably of an alkali metal, such as Na or K.

The esterification is advantageously carried out in the presence of an inert solvent. Particularly suitable solvents are ethers, such as diethyl ether, di-n-butyl ether, tetrahydrofuran, dioxane or anisole, ketones, such as acetone, butanone or cyclohexanone, amides, such as dimethylformamide or hexamethylphosphoric triamide, hydrocarbons, such as benzene, toluene or xylene, halogenohydrocarbons, such as carbon tetrachloride or tetrachloroethylene, and sulfoxides, such as dimethyl sulfoxide or sulfolane. Water-immiscible solvents can at the same time advantageously be used for azeotropic distillation of the water formed during the esterification. Occasionally, it is also possible to use an excess of an organic base, for example pyridine, quinoline or triethylamine, as a solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are as a rule complete after 15 minutes to 48 hours.

The specific reaction conditions for the esterification depend substantially on the nature of the starting materials used. Thus, a free carboxylic acid is reacted with a free alcohol or phenol as a rule in the presence of a strong acid, for example a mineral acid, such as hydrochloric acid or sulfuric acid. A preferred reaction procedure comprises reacting an acid anhydride or, in particular, an acid chloride with an alcohol, preferably in a basic medium, particularly important bases being alkali metal hydroxides, such as sodium hydroxide or potassium hydroxide, alkali metal carbonates and bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, and organic bases, such as triethylamine, pyridine, lutidine, collidine or quinoline. In another preferred embodiment of the esterification, the alcohol or the phenol is first converted to the sodium or potassium alcoholate or phenolate, for example by treatment with ethanolic sodium hydroxide or potassium hydroxide solution, the product is isolated and, together with sodium bicarbonate or potassium carbonate, is suspended in acetone or diethyl ether, with stirring, and this suspension is treated with a solution of the acid chloride or of the anhydride in diethyl ether, acetone or dimethylformamide, advantageously at temperatures between about −25° and +20°.

Dioxane derivatives of the formula I (in which one of the groups $A^1$ and/or $A^2$ is a 1,3-dioxane-2,5-diyl group) are advantageously prepared by reacting an appropriate aldehyde, for example an aldehyde of the formula $R^1$—$(A^1)_{m-1}$—CHO, $R^1$—$(A^1)_m$—$Z^1$—A—$Z^2$—CHO, O=CH—$(A^1)_{m-1}$—$Z^1$—A—$(Z^2$—$A^2)_n$—$R^2$ or O=CH—$R^2$ (or one of its reactive derivatives) with an appropriate 1,3-diol, for example a diol of the formula $(HOCH_2)_2CH$—$(A^1)_{m-1}$—$Z^1$—A—$(Z^2$—$A^2)_n$—$R^2$, $(HOCH_2)_2CH$—$R^2$, $R^1$—$(A^1)_{m-1}$—$CH(CH_2OH)_2$ or $R^1$—$(A^1)_m$—$Z^1$—A—$Z^2CH(CH_2OH)_2$ (or one of its reactive derivatives), preferably in the presence of an inert solvent, such as benzene or toluene, and/or of a catalyst, for example a strong acid, such as sulfuric acid, benzenesulfonic acid or p-toluenesulfonic acid, at temperatures between about 20° and about 150°, preferably between 80° and 120°. Suitable reactive derivatives of the starting materials are primarily acetals, for example those of the formulae $R^1$—$(A^1)_{m-1}CH(OR^3)_2$, $R^1$—$(A^1)_m$—$Z^1$—A—$Z^2$—$CH(OR^3)_2$, $(R^3O)_2CH$—$(A^1)_{m-1}$—$Z^1$—A—$(Z^2$—$A^2)_n$—$R^2$, $(R^3O)_2$—$R^2$, $R^4$—$CH(OCH_2)_2CH$—$(A^1)_{m-1}$—$Z^1$—A—$(Z^2$—$A^2)_n$—$R^2$, $R^4$—$CH(OCH_2)_2CH$—$R^2$, $R^1$—$(A^1)_{m-1}$—$CH(CH_2O)_2CH$—$R^4$ or $R^1$—$(A^1)_m$—$Z^1$—A—$Z^1CH(CH_2O)_2$—$CHR^4$, in which $R^3$ is alkyl having 1-4 C atoms, two radicals $R^3$ together may furthermore be alkylene having 2 or 3 C atoms, and $R^4$ is H, alkyl having 1-4 C atoms or phenyl.

Some of the stated aldehydes and 1,3-diols and their reactive derivatives are known, and some of them can be prepared without difficulty from compounds known from the literature, using standard methods of organic chemistry. For example, the aldehydes are obtainable by oxidation of the corresponding alcohols or by reduction of corresponding carboxylic acids or their derivatives, or the diols are obtainable by reduction of the corresponding diesters.

Nitriles of the formula I (in which $R^1$ and/or $R^2$ are CN and/or $A^1$ and/or $A^2$ is substituted by at least one CN group) can be prepared by dehydrating appropriate acid amides, for example those which contain a $CONH_2$ group in place of the radical X. The amides are obtainable, for example, from the corresponding esters or acid halides by reaction with ammonia. Examples of suitable agents which eliminate water are inorganic acid chlorides, such as $SOCl_2$, $PCl_3$, $PCl_5$, $POCl_3$, $SO_2Cl_2$ and $COCl_2$, as well as $P_2O_5$, $P_2S_5$, $AlCl_3$ (for example as a double compound with NaCl), aromatic sulfonic acids and sulfonyl halides. The reaction can be carried out in the presence or absence of an inert solvent at temperatures between about 0° and 150°; examples of suitable solvents are bases, such as pyridine or triethylamine, aromatic hydrocarbons, such as benzene, toluene or xylene, and amides, such as dimethylformamide.

The abovementioned nitriles of the formula I can also be prepared by reacting appropriate acid halides, preferably the chlorides, with sulfamide, advantageously in an inert solvent, such as tetramethylene sulfone, at temperatures between about 80° and 150°, preferably at 120°. After the usual working-up procedure, the nitriles can be isolated directly.

Compounds of the formula I are furthermore obtainable by condensing a thiophene derivative of the formula II

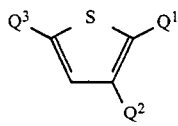

in which one of the radicals $Q^1$ and $Q^2$ is —CHO and the other is —SCH$_2$—$Q^3$, and $Q^3$ is $R^1$—$(A^1)_m$—$Z^1$— or $R^2$—$(A^2$—$Z^2)_n$—.

The preparation of the compounds of the formula II and their condensation can be carried out by methods which are known per se, as described in the literature [for example V. P. Litvinov and Ya. L. Gold'farb, Izv. Akad. Nauk. SSSR, Ser. Khim., 2183 (1963)], the reaction conditions employed being those which are conventionally used and suitable for the stated reactions. In this context, it is also possible to use variants which are known per se but are not specifically mentioned here.

Ethers of the formula I (in which $R^1$ and/or $R^2$ are alkyl groups, in which one or two CH$_2$ groups are replaced by O atoms, and/or in which $Z^1$ and/or $Z^2$ are —OCH$_2$— or —CH$_2$O— groups) are obtainable by etherification from appropriate hydroxy compounds, preferably appropriate phenols, the hydroxy compound advantageously first being converted to an appropriate metal derivative, for example to the corresponding alkali metal alcoholate or alkali metal phenolate by treatment with NaH, NaNH$_2$, NaOH, KOH, Na$_2$CO$_3$ or K$_2$CO$_3$. This product can then be reacted with the appropriate alkyl halide or sulfonate or dialkyl sulfate, advantageously in an inert solvent, such as acetone, 1,2-dimethoxyethane, dimethylformamide or dimethyl sulfoxide, or even in an excess of aqueous or aqueous alcoholic NaOH or KOH, at temperatures between about 20° and 100°.

Nitriles of the formula I (in which $R^1$ and/or $R^2$ are CN and/or in which $A^1$ and/or $A^2$ is substituted by at least one CN group) can furthermore be prepared by reacting appropriate chlorine or bromine compounds of the formula I (in which $R^1$ and/or $R^2$ is Cl or Br and/or in which $A^1$ and/or $A^2$ is substituted by at least one Cl or Br atom), with a cyanide, advantageously with a metal cyanide, such as NaCN, KCN or Cu$_2$(CN)$_2$, for example in the presence of pyridine in an inert solvent, such as dimethylformamide or N-methylpyrrolidone, at temperatures between 20° and 200°.

The liquid crystalline phases according to the invention comprise at least two liquid-crystal components, wherein at least one is a compound having the structure wing group-ring-(bridging element-ring)$_{(1-3)}$-wing group wherein the ring groups, the bridging elements and at least one ring are conventional structural elements in liquid crystal compounds, wherein one ring is of the formula

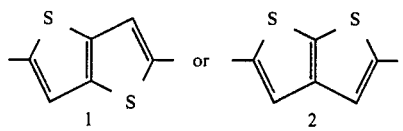

and said at least one compound is present in an amount effective to improve the elastic properties of the phase. These phases preferably comprise 2 to 15, in particular 3 to 12, components and preferably at least one compound of the formula I.

In other components are preferably chosen from the nematic or nematogenic substances, in particular the known substances, from the classes comprising the azoxybenzenes, benzylideneanilines, biphenyls, terphenyls, phenyl benzoates, cyclohexyl benzoates, phenyl cyclohexanecarboxylate, cyclohexyl cyclohexanecarboxylate, phenylcyclohexanes, cyclohexylbiphenyls, cyclohexylcyclohexanes, cyclohexylnaphthalenes, 1,4-bis-cyclohexylbenzenes, 4,4'-biscyclohexylbiphenyls, phenylpyrimidines, cyclohexylpyrimidines, phenylpyridazines, cyclohexylpyridazines, phenyldioxanes, cyclohexyldioxanes, phenyldithianes, cyclohexyldithianes, stilbenes which may or may not be halogenated, benzyl phenyl ether, tolanes and substituted cinnamic acids.

The most important compounds which can be used as components of such liquid crystalline phases can be characterised by the formula VI $$R'—L—G—E—R'' \qquad \text{VI}$$

in which L and E are each a carbocyclic or heterocyclic ring system obtained from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| G | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals may furthermore be CN, NC, NO$_2$, CF$_3$, F, Cl or Br.

In most of these compounds, R' and R'' differ from one another, one of these radicals generally being an alkyl or alkoxy group. However, other variants of the substituents envisaged are also commonly used. Many such substances, or mixtures thereof, are available commercially. All of these substances can be prepared by methods known from the literature.

The phases according to the invention contain about 0.1 to 99, preferably 10 to 90, % of one or more compounds of the formula I. Other preferred phases according to the invention are those containing 0.1 to 70, in particular 0.5 to 60, % of one or more compounds of the formula I.

The phases according to the invention are prepared in a conventional manner. As a rule, the components are dissolved, one in the other, advantageously at elevated temperature.

By means of suitable additives, the liquid crystalline phases according to the invention can be modified so that they can be used in all types of liquid crystal display elements disclosed to date.

Additives of this type are known to those skilled in the art, and are described in detail in the literature. For example, it is possible to add conductive salts, preferably ethyl-dimethyl-dodecyl-ammonium 4-hexyloxybenzoate, tetrabutylammonium tetraphenylboranate or complex salts of crown ethers (cf. for example I. Haller et al., Mol. Cryst. Liq. Cryst. volume 24, pages 249–258 (1973)), for improving the conductivity, dichroic dyes for producing colored guest-host systems, or substances for altering the dielectric anisotropy, the viscosity and/or the orientation of the nematic phases. Substances of this type are described in, for example, German Offenlegungsschriften Nos. 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. is the melting point and c.p. is the clear point of a liquid crystal substance.

"Usual working-up procedure" means the following: water is added, the mixture is extracted with methylene chloride, the phases are separated, the organic phase is dried and evaporated down, and the product is purified by crystallization and/or chromatography.

EXAMPLE 1

3.5 g of 5-n-pentyl-thieno[3,2-b]thiophene-2-carboxylic acid chloride [obtainable by reacting 5-n-pentyl-thieno[3,2-b]thiophene-5-carboxylic acid (m.p. 156°, c.p. 196°) with thionyl chloride] in 20 ml of toluene are added dropwise to a mixture of 2.25 g of 4-n-pentylphenol, 1.08 g of pyridine and 30 ml of toluene, the mixture is heated to the boil for 2 hours and allowed to cool, the pyridine hydrochloride is filtered off, and the mixture is worked up in the usual manner. 4-n-Pentylphenyl 5-n-pentyl-thieno[3,2-b]thiophene-2-carboxylate of melting point 58° and clear point 93° is obtained.

The following compounds are prepared analogously:
4-ethylphenyl 5-pentyl-thieno[3,2-b]thiophene-2-carboxylate,
4-propylphenyl 5-pentyl-thieno[3,2-b]thiophene-2-carboxylate,
4-butylphenyl 5-phenyl-thieno[3,2-b]thiophene-2-carboxylate,
4-heptylphenyl 5-pentyl-thieno[3,2-b]thiophene-2-carboxylate,
4-ethylphenyl 5-propyl-thieno[3,2-b]thiophene-2-carboxylate,
4-propylphenyl 5-propyl-thieno[3,2-b]thiophene-2-carboxylate,
4-butylphenyl 5-propyl-thieno[3,2-b]thiophene-2-carboxylate,
4-pentylphenyl 5-propyl-thieno[3,2-b]thiophene-2-carboxylate,
4-heptylphenyl 5-propyl-thieno[3,2-b]thiophene-2-carboxylate,
4-ethylphenyl 5-butyl-thieno[3,2-b]thiophene-2-carboxylate,
4-propylphenyl 5-butyl-thieno[3,2-b]thiophene-2-carboxylate,
4-butylphenyl 5-butyl-thieno[3,2-b]thiophene-2-carboxylate,
4-pentylphenyl 5-butyl-thieno[3,2-b]thiophene-2-carboxylate,
4-heptylphenyl 5-butyl-thieno[3,2-b]thiophene-2-carboxylate,
4-ethylphenyl 5-heptyl-thieno[3,2-b]thiophene-2-carboxylate,
4-propylphenyl 5-heptyl-thieno[3,2-b]thiophene-2-carboxylate,
4-butylphenyl 5-heptyl-thieno[3,2-b]thiophene-2-carboxylate,
4-pentylphenyl 5-heptyl-thieno[3,2-b]thiophene-2-carboxylate,
4-heptylphenyl 5-heptyl-thieno[3,2-b]thiophene-2-carboxylate,
4-ethylphenyl 5-nonyl-thieno[3,2-b]thiophene-2-carboxylate,
4-propylphenyl 5-nonyl-thieno[3,2-b]thiophene-2-carboxylate,
4-butylphenyl 5-nonyl-thieno[3,2-b]thiophene-2-carboxylate,
4-pentylphenyl 5-nonyl-thieno[3,2-b]thiophene-2-carboxylate,
4-heptylphenyl 5-nonyl-thieno[3,2-b]thiophene-2-carboxylate,
4-cyanophenyl 5-propyl-thieno[3,2-b]thiophene-2-carboxylate,
4-cyanophenyl 5-butyl-thieno[3,2-b]thiophene-2-carboxylate,
4-cyanophenyl 5-pentyl-thieno[3,2-b]thiophene-2-carboxylate, m.p. 98°, c.p. 137°,
4-cyanophenyl 5-hexyl-thieno[3,2-b]thiophene-2-carboxylate,
4-cyanophenyl 5-heptyl-thieno[3,2-b]thiophene-2-carboxylate,
4-cyanophenyl 5-nonyl-thieno[3,2-b]thiophene-2-carboxylate,
4-fluorophenyl 5-pentyl-thieno[3,2-b]thiophene-2-carboxylate,
4-chlorophenyl 5-pentyl-thieno[3,2-b]thiophene-2-carboxylate, 4-bromophenyl 5-pentyl-thieno[3,2-b]thiophene-2-carboxylate,
4-methoxyphenyl 5-pentyl-thieno[3,2-b]thiophene-2-carboxylate,
4-ethoxyphenyl 5-pentyl-thieno[3,2-b]thiophene-2-carboxylate,
4-propoxyphenyl 5-pentyl-thieno[3,2-b]thiophene-2-carboxylate,
4-butoxyphenyl 5-pentyl-thieno[3,2-b]thiophene-2-carboxylate,
4-pentyloxyphenyl 5-pentyl-thieno[3,2-b]thiophene-2-carboxylate,
4-heptyloxyphenyl 5-pentyl-thieno[3,2-b]thiophene-2-carboxylate,
4-nonyloxyphenyl 5-pentyl-thieno[3,2-b]thiophene-2-carboxylate,
4'-propylbiphenylyl 5-pentyl-thieno[3,2-b]thiophene-2-carboxylate,
4'-cyanobiphenylyl 5-pentyl-thieno[3,2-b]thiophene-2-carboxylate,
2'-fluoro-4'-ethylbiphenylyl 5-pentyl-thieno[3,2-b]thiophene-2-carboxylate,
2-methyl-4'-propylbiphenylyl 5-pentyl-thieno[3,2-b]thiophene-2-carboxylate,
4-(4-propylcyclohexyl)-phenyl 5-pentyl-thieno[3,2-b]thiophene-2-carboxylate,
4-(1-cyano-4-propylcyclohexyl)-phenyl 5-pentyl-thieno[3,2-b]thiophene-2-carboxylate and
4-(5-propyl-1,3-dioxan-2-yl)-phenyl 5-pentyl-thieno[3,2-b]thiophene-2-carboxylate.
trans-4-ethylcyclohexyl 5-pentyl-thieno[3,2-b]thiophene-2-carboxylate,
trans-4-propylcyclohexyl 5-pentyl-thieno[3,2-b]thiophene-2-carboxylate, M.p. 45°, c.p. 93°
trans-4-butylcyclohexyl 5-pentyl-thieno[3,2-b]thiophene-2-carboxylate,
trans-4-pentylcyclohexyl 5-pentyl-thieno[3,2-b]thiophene-2-carboxylate,
trans-4-heptylcyclohexyl 5-pentyl-thieno[3,2-b]-thiophene-2-carboxylate,
trans-4-ethylcyclohexyl 5-propyl-thieno[3,2-b]thiophene-2-carboxylate,
trans-4-propylcyclohexyl 5-propyl-thieno[3,2-b]thiophene-2-carboxylate,
trans-4-butylcyclohexyl 5-propyl-thieno[3,2-b]thiophene-2-carboxylate,
trans-4-pentylcyclohexyl 5-propyl-thieno[3,2-b]thiophene-2-carboxylate,
trans-4-heptylcyclohexyl 5-propyl-thieno[3,2-b]thiophene-2-carboxylate,
trans-4-ethoxycyclohexyl 5-propyl-thieno[3,2-b]thiophene-2-carboxylate,
trans-4-butoxycyclohexyl 5-propyl-thieno[3,2-b]thiophene-2-carboxylate,
trans,trans-4-ethylbicyclohex-4'-yl 5-propyl-thieno[3,2-b]thiophene-2-carboxylate
trans,trans-4-propylbicyclohex-4'-yl 5-propyl-thieno[3,2-b]thiophene-2-carboxylate
trans,trans-4-butylbicyclohex-4'-yl 5-propyl-thieno[3,2-b]thiophene-2-carboxylate
trans,trans-4-pentylbicyclohex-4'-yl 5-propyl-thieno[3,2-b]thiophene-2-carboxylate
trans,trans-4-heptylbicyclohex-4'-yl 5-propyl-thieno[3,2-b]thiophene-2-carboxylate
trans,trans-4-ethoxybicyclohex-4'-yl 5-propyl-thieno[3,2-b]thiophene-2-carboxylate
trans,trans-4-butoxybicyclohex-4'-yl 5-propyl-thieno[3,2-b]thiophene-2-carboxylate
trans,trans-4-propionyloxybicyclohex-4'-yl 5-propyl-thieno[3,2-b]thiophene-2-carboxylate

EXAMPLE 2

5.75 g of 2-[2-(trans-5-n-pentylcyclohexyl)-acetyl]-5-n-pentylthieno[3,2-b]thiophene [obtainable by reacting 5-n-pentylthieno[3,2-b]thiophene-2-carbonitrile (obtained from the acid chloride by reaction with ammonia followed by dehydration of the amide with thionyl chloride) with a Grignard solution prepared from trans-4-bromomethyl-n-pentylcyclohexane] are boiled with 2.5 g of 85% hydrazine hydrate, 3.2 g of potassium hydroxide and 15 ml of triethylene glycol for 2 hours, and then heated in an apparatus possessing a descending condenser until the internal temperature reaches 195° C., and kept at this temperature for 4 hours. Cooling, dilution with water and the usual working-up procedure give 4.1 g of 1-trans-4-pentylcyclohexyl-2-[pentylthieno[3,2-b]thien-2-yl]-ethane.

The following compounds are prepared analogously:
1-trans-4-methylcyclohexyl-2-[5-pentylthieno[3,2-b]thien-2-yl]-ethane
1-trans-4-ethylcyclohexyl-2-[5-pentylthieno[3,2-b]thien-2-yl]-ethane
1-trans-4-propylcyclohexyl-2-[5-pentylthieno[3,2-b]thien-2-yl]-ethane
1-trans-4-butylcyclohexyl-2-[5-pentylthieno[3,2-b]thien-2-yl]-ethane
1-trans-4-heptylcyclohexyl-2-[5-pentylthieno[3,2-b]thien-2-yl]-ethane
1-trans-4-nonylcyclohexyl-2-[5-pentylthieno[3,2-b]thien-2-yl]-ethane
1-trans-4-methylcyclohexyl-2-[5-propylthieno[3,2-b]thien-2-yl]-ethane
1-trans-4-ethylcyclohexyl-2-[5-propylthieno[3,2-b]thien-2-yl]-ethane
1-trans-4-propylcyclohexyl-2-[5-propylthieno[3,2-b]thien-2-yl]-ethane
1-trans-4-butylcyclohexyl-2-[5-propylthieno[3,2-b]thien-2-yl]-ethane
1-trans-4-pentylcyclohexyl-2-[5-propylthieno[3,2-b]thien-2-yl]-ethane
1-trans-4-heptylcyclohexyl-2-[5-propylthieno[3,2-b]thien-2-yl]-ethane
1-trans-4-nonylcyclohexyl-2-[5-propylthieno[3,2-b]thien-2-yl]-ethane
1-trans-4-methylcyclohexyl-2-[5-heptylthieno[3,2-b]thien-2-yl]-ethane
1-trans-4-ethylcyclohexyl-2-[5-heptylthieno[3,2-b]thien-2-yl]-ethane
1-trans-4-propylcyclohexyl-2-[5-heptylthieno[3,2-b]thien-2-yl]-ethane
1-trans-4-butylcyclohexyl-2-[5-heptylthieno[3,2-b]thien-2-yl]-ethane
1-trans-4-pentylcyclohexyl-2-[5-heptylthieno[3,2-b]thien-2-yl]-ethane
1-trans-4-heptylcyclohexyl-2-[5-heptylthieno[3,2-b]thien-2-yl]-ethane
1-trans-4-nonylcyclohexyl-2-[5-heptylthieno[3,2-b]thien-2-yl]-ethane
1-trans-4-methylcyclohexyl-2-[5-(p-propylphenyl)-thieno[3,2-b]thien-2-yl]-ethane
1-trans-4-ethylcyclohexyl-2-[5-(p-propylphenyl)-thieno[3,2-b]thien-2-yl]-ethane
1-trans-4-propylcyclohexyl-2-[5-(p-propylphenyl)-thieno[3,2-b]thien-2-yl]-ethane
1-trans-4-butylcyclohexyl-2-[5-(p-propylphenyl)-thieno[3,2-b]thien-2-yl]-ethane 1-trans-4-pentylcyclohexyl-2-[5-(p-propylphenyl)-thieno[3,2-b]thien-2-yl]-ethane
1-trans-4-heptylcyclohexyl-2-[5-(p-propylphenyl)-thieno[3,2-b]thien-2-yl]-ethane
1-trans-4-methylcyclohexyl-2-[5-(p-cyanophenyl)-thieno[3,2-b]thien-2-yl]-ethane
1-trans-4-ethylcyclohexyl-2-[5-(p-cyanophenyl)-thieno[3,2-b]thien-2-yl]-ethane
1-trans-4-propylcyclohexyl-2-[5-(p-cyanophenyl)-thieno[3,2-b]thien-2-yl]-ethane
1-trans-4-butylcyclohexyl-2-[5-(p-cyanophenyl)-thieno[3,2-b]thien-2-yl]-ethane
1-trans-4-pentylcyclohexyl-2-[5-(p-cyanophenyl)-thieno[3,2-b]thien-2-yl]-ethane
1-trans-4-heptylcyclohexyl-2-[5-(p-cyanophenyl)-thieno[3,2-b]thien-2-yl]-ethane
1-trans-4-methylcyclohexyl-2-[5-(p-butoxyphenyl)-thieno[3,2-b]thien-2-yl]-ethane
1-trans-4-ethylcyclohexyl-2-[5-(p-butoxyphenyl)-thieno[3,2-b]thien-2-yl]-ethane
1-trans-4-propylcyclohexyl-2-[5-(p-butoxyphenyl)-thieno[3,2-b]thien-2-yl]-ethane
1-trans-4-butylcyclohexyl-2-[5-(p-butoxyphenyl)-thieno[3,2-b]thien-2-yl]-ethane
1-trans-4-pentylcyclohexyl-2-[5-(p-butoxyphenyl)-thieno[3,2-b]thien-2-yl]-ethane
1-trans-4-heptylcyclohexyl-2-[5-(p-butoxyphenyl)-thieno[3,2-b]thien-2-yl]-ethane
1-trans-4-methylcyclohexyl-2-[5-(5-propylpyrimidin-2-yl)-thieno[3,2-b]thien-2-yl]-ethane
1-trans-4-ethylcyclohexyl-2-[5-(5-propylpyrimidin-2-yl)-thieno[3,2-b]thien-2-yl]-ethane
1-trans-4-propylcyclohexyl-2-[5-(5-propylpyrimidin-2-yl)-thieno[3,2-b]thien-2-yl]-ethane
1-trans-4-butylcyclohexyl-2-[5-(5-propylpyrimidin-2-yl)-thieno[3,2-b]thien-2-yl]-ethane
1-trans-4-pentylcyclohexyl-2-[5-(5-propylpyrimidin-2-yl)-thieno[3,2-b]thien-2-yl]-ethane
1-trans-4-heptylcyclohexyl-2-[5-(5-propylpyrimidin-2-yl)-thieno[3,2-b]thien-2-yl]-ethane
1-p-ethylphenyl-2-[5-pentyl-thieno[2,3-b]thien-2-yl]-ethane
1-p-butylphenyl-2-[5-pentyl-thieno[2,3-b]thien-2-yl]-ethane
1-p-pentylphenyl-2-[5-pentyl-thieno[2,3-b]thien-2-yl]-ethane
1-p-heptylphenyl-2-[5-pentyl-thieno[2,3-b]thien-2-yl]-ethane
1-p-cyanophenyl-2-[5-pentyl-thieno[2,3-b]thien-2-yl]-ethane
1-p-fluorophenyl-2-[5-pentyl-thieno[2,3-b]thien-2-yl]-ethane
1-p-chlorophenyl-2-[5-pentyl-thieno[2,3-b]thien-2-yl]-ethane
1-4-ethylcyclohexyl-2-[5-pentyl-thieno[2,3-b]thien-2-yl]-ethane
1-4-propylcyclohexyl-2-[5-pentyl-thieno[2,3-b]thien-2-yl]-ethane
1-4-butylcyclohexyl-2-[5-pentyl-thieno[2,3-b]thien-2-yl]-ethane
1-4-pentylcyclohexyl-2-[5-pentyl-thieno[2,3-b]thien-2-yl]-ethane and
1-4-heptylcyclohexyl-2-[5-pentyl-thieno[2,3-b]thien-2-yl]-ethane.

EXAMPLE 3

A solution of 4.6 g of 3-p-cyanobenzylmercapto-2-formyl-5-(4-pentylcyclohexyl)-thiophene in 25 ml of ethanol is added dropwise, at room temperature and in the course of 5 minutes, to an alcoholate solution prepared from 1.9 g of sodium and 60 ml of ethanol, and the mixture is then boiled for 5 hours. The usual working-up procedure gives 2-p-cyanophenyl-5-(4-pentylcyclohexyl)-thieno[3,2-b]thiophene.

The following compounds are prepared analogously:
2-p-cyanophenyl-5-(4-propylcyclohexyl)-thieno[3,2-b]thiophene,
2-p-cyanophenyl-5-(4-butylcyclohexyl)-thieno[3,2-b]thiophene,
2-p-cyanophenyl-5-(4-heptylcyclohexyl)-thieno[3,2-b]thiophene,
2-p-cyanophenyl-5-(4'-propylcyclohexylcyclohexyl)-thieno[3,2-b]thiophene,
2-p-cyanophenyl-5-(4'-butylcyclohexylcyclohexyl)-thieno[3,2-b]thiophene,
2-p-cyanophenyl-5-(4'-pentylcyclohexylcyclohexyl)-thieno[3,2-b]thiophene,
2-p-cyanophenyl-5-(4'-heptylcyclohexylcyclohexyl)-thieno[3,2-b]thiophene,
2-p-cyanophenyl-5-(p-4-propylcyclohexylphenyl)-thieno[3,2-b]thiophene,
2-p-cyanophenyl-5-(p-4-butylcyclohexylphenyl)-thieno[3,2-b]thiophene,
2-p-cyanophenyl-5-(p-4-pentylcyclohexylphenyl)-thieno[3,2-b]thiophene and
2-p-cyanophenyl-5-(p-4-heptylcyclohexylphenyl)-thieno[3,2-b]thiophene.

EXAMPLE 4

20.5 g of 5-n-heptyl-3-chlorothieno[3,2-b]thiophene-2-carboxylic acid chloride [obtainable by reacting 5-n-heptylthiophene-2-acrylic acid (obtained from 5-n-heptyl-thiophene-2-carbaldehyde and malonic acid in the presence of pyridine/piperidine) with thionyl chloride/pyridine in toluene] are heated to 100° for 4 hours with 13.6 g of 4-n-propylphenol and 8 g of pyridine in 100 ml of toluene. The usual working-up procedure gives 14.8 g of 4-n-propylphenyl 5-n-heptyl-3-chlorothieno[3,2-b]thiophene-2-carboxylate.

The following compounds are prepared analogously:
4-ethylphenyl 5-n-heptyl-3-chlorothieno[3,2-b]thiophene-2-carboxylate,
4-butylphenyl 5-n-heptyl-3-chlorothieno[3,2-b]thiophene-2-carboxylate,
4-pentylphenyl 5-n-heptyl-3-chlorothieno[3,2-b]thiophene-2-carboxylate,
4-heptylphenyl 5-n-heptyl-3-chlorothieno[3,2-b]thiophene-2-carboxylate,
4-nonylphenyl 5-n-heptyl-3-chlorothieno[3,2-b]thiophene-2-carboxylate,
4-cyanophenyl 5-n-heptyl-3-chlorothieno[3,2-b]thiophene-2-carboxylate,
4-fluorophenyl 5-n-heptyl-3-chlorothieno[3,2-b]thiophene-2-carboxylate,
4-ethylcyclohexyl 5-n-heptyl-3-chlorothieno[3,2-b]thiophene-2-carboxylate,
4-propylcyclohexyl 5-n-heptyl-3-chlorothieno[3,2-b]thiophene-2-carboxylate,
4-butylcyclohexyl 5-n-heptyl-3-chlorothieno[3,2-b]thiophene-2-carboxylate,
4-pentylcyclohexyl 5-n-heptyl-3-chlorothieno[3,2-b]thiophene-2-carboxylate,
4-heptylcyclohexyl 5-n-heptyl-3-chlorothieno[3,2-b]thiophene-2-carboxylate and
4-nonylcyclohexyl 5-n-heptyl-3-chlorothieno[3,2-b]thiophene-2-carboxylate.

EXAMPLE 5

20.4 g of 5-n-octylthieno[2,3-b]thiophene-2-carbaldehyde (obtainable from 2-n-octylthieno[2,3-b]thiophene by Vilsmeyer formylation with phosphorus oxychloride/dimethylformamide) and 9.5 g of 2-n-pentylpropane-1,3-diol are dissolved in 150 ml of toluene, a pinch of toluenesulfonic acid is added, and the mixture is heated under a water separator until water is no longer separated off. The acid is washed out with sodium bicarbonate solution, the organic phase is dried over sodium sulfate, and the toluene is distilled off. The pure trans-2-(5-n-octylthieno[2,3-b]thien-2-yl)-5-n-pentyl-1,3-dioxane is obtained by repeated recrystallization from ethanol (17.5 g).

The following compounds are prepared analogously:
2-(5-n-octylthieno[2,3-b]thien-2-yl)-5-ethyl-1,3-dioxane,
2-(5-n-octylthieno[2,3-b]thien-2-yl)-5-propyl-1,3-dioxane,
2-(5-n-octylthieno[2,3-b]thien-2-yl)-5-butyl-1,3-dioxane,
2-(5-n-octylthieno[2,3-b]thien-2-yl)-5-heptyl-1,3-dioxane,
2-(5-n-octylthieno[2,3-b]thien-2-yl)-5-nonyl-1,3-dioxane,
2-(5-n-pentylthieno[2,3-b]thien-2-yl)-5-ethyl-1,3-dioxane,
2-(5-n-pentylthieno[2,3-b]thien-2-yl)-5-propyl-1,3-dioxane,
2-(5-n-pentylthieno[2,3-b]thien-2-yl)-5-butyl-1,3-dioxane,
2-(5-n-pentylthieno[2,3-b]thien-2-yl)-5-pentyl-1,3-dioxane, M.p. 86°, c.p. 84,5° (monotropic)
2-(5-n-pentylthieno[2,3-b]thien-2-yl)-5-heptyl-1,3-dioxane,
2-(5-n-pentylthieno[2,3-b]thien-2-yl)-5-nonyl-1,3-dioxane,
2-(5-n-propylthieno[2,3-b]thien-2-yl)-5-ethyl-1,3-dioxane,
2-(5-n-propylthieno[2,3-b]thien-2-yl)-5-propyl-1,3-dioxane,
2-(5-n-propylthieno[2,3-b]thien-2-yl)-5-butyl-1,3-dioxane,
2-(5-n-propylthieno[2,3-b]thien-2-yl)-5-pentyl-1,3-dioxane,
2-(5-n-propylthieno[2,3-b]thien-2-yl)-5-heptyl-1,3-dioxane,
2-(5-n-propylthieno[2,3-b]thien-2-yl)-5-nonyl-1,3-dioxane,
2-(5-cyanothieno[2,3-b]thien-2-yl)-5-ethyl-1,3-dioxane,
2-(5-cyanothieno[2,3-b]thien-2-yl)-5-propyl-1,3-dioxane,
2-(5-cyanothieno[2,3-b]thien-2-yl)-5-butyl-1,3-dioxane,
2-(5-cyanothieno[2,3-b]thien-2-yl)-5-pentyl-1,3-dioxane,
2-(5-cyanothieno[2,3-b]thien-2-yl)-5-heptyl-1,3-dioxane,
2-(5-cyanothieno[2,3-b]thien-2-yl)-5-nonyl-1,3-dioxane,
2-(5-cyanothieno[2,3-b]thien-2-yl)-5-(4-ethylcyclohexyl)-1,3-dioxane,
2-(5-cyanothieno[2,3-b]thien-2-yl)-5-(4-propylcyclohexyl)-1,3-dioxane,
2-(5-cyanothieno[2,3-b]thien-2-yl)-5-(4-butylcyclohexyl)-1,3-dioxane,
2-(5-cyanothieno[2,3-b]thien-2-yl)-5-(4-pentylcyclohexyl)-1,3-dioxane,
2-(5-cyanothieno[2,3-b]thien-2-yl)-5-(4-heptylcyclohexyl)-1,3-dioxane, and
2-(5-cyanothieno[2,3-b]thien-2-yl)-5-(4-nonylcyclohexyl)-1,3-dioxane.

EXAMPLE 6

19 g of 2-[4-(trans-4-n-propylcyclohexyl)-styryl]-5-n-pentylthiophene (obtainable by Friedel Crafts acylation of 2-pentylthiophene with 4-(trans-4-n-propylcyclohexyl)-phenylacetyl chloride and reduction of the resulting ketone with sodium boranate to give the alcohol, followed by dehydration) and 5 g of sulfur are heated to 220° for 3 hours. Subsequent working-up by chromatography gives 8.3 g of 2-[4-trans-4-n-propylcyclohexylphenyl]-5-n-pentylthieno[3,2-b]thiophene.

The following compounds are prepared analogously:
2-[4-(trans-4-ethylcyclohexyl)-phenyl]-5-n-pentylthieno[3,2-b]thiophene,
2-[4-(trans-4-butylcyclohexyl)-phenyl]-5-n-pentylthieno[3,2-b]thiophene,
2-[4-(trans-4-pentylcyclohexyl)-phenyl]-5-n-pentylthieno[3,2-b]thiophene,
2-[4-(trans-4-heptylcyclohexyl)-phenyl]-5-n-pentylthieno[3,2-b]thiophene,
2-[4-(trans-4-nonylcyclohexyl)-phenyl]-5-n-pentylthieno[3,2-b]thiophene,
2-[4-(trans-4-ethylcyclohexyl)-phenyl]-5-n-heptylthieno[3,2-b]thiophene,
2-[4-(trans-4-butylcyclohexyl)-phenyl]-5-n-heptylthieno[3,2-b]thiophene,
2-[4-(trans-4-pentylcyclohexyl)-phenyl]-5-n-heptylthieno[3,2-b]thiophene,
2-[4-(trans-4-heptylcyclohexyl)-phenyl]-5-n-heptylthieno[3,2-b]thiophene,
2-[4-(trans-4-nonylcyclohexyl)-phenyl]-5-n-heptylthieno[3,2-b]thiophene,
2-[4-(trans-4-ethylcyclohexyl)-phenyl]-5-cyanothieno[3,2-b]thiophene,
2-[4-(trans-4-butylcyclohexyl)-phenyl]-5-cyanothieno[3,2-b]thiophene,
2-[4-(trans-4-pentylcyclohexyl)-phenyl]-5-cyanothieno[3,2-b]thiophene,
2-[4-(trans-4-heptylcyclohexyl)-phenyl]-5-cyanothieno[3,2-b]thiophene,
2-[4-(trans-4-nonylcyclohexyl)-phenyl]-5-cyanothieno[3,2-b]thiophene,
2-[trans,trans-4'-ethylcyclohexylcyclohexyl]-5-cyanothieno[3,2-b]thiophene,
2-[trans,trans-4'-butylcyclohexylcyclohexyl]-5-cyanothieno[3,2-b]thiophene,
2-[trans,trans-4'-pentylcyclohexylcyclohexyl]-5-cyanothieno[3,2-b]thiophene,
2-[trans,trans-4'-heptylcyclohexylcyclohexyl]-5-cyanothieno[3,2-b]thiophene and
2-[trans,trans-4'-nonylcyclohexylcyclohexyl]-5-cyanothieno[3,2-b]thiophene.
2-(p-ethylphenyl)-5-propylthieno[3,2-b]thiophene
2-(p-propylphenyl)-5-propylthieno[3,2-b]thiophene
2-(p-butylphenyl)-5-propylthieno[3,2-b]thiophene
2-(p-pentylphenyl)-5-propylthieno[3,2-b]thiophene
2-(p-heptylphenyl)-5-propylthieno[3,2-b]thiophene
2-(p-cyanophenyl)-5-propylthieno[3,2-b]thiophene
2-(p-methoxyphenyl)-5-propylthieno[3,2-b]thiophene
2-(p-ethoxyphenyl)-5-propylthieno[3,2-b]thiophene
2-(p-butoxyphenyl)-5-propylthieno[3,2-b]thiophene
2-(p-pentoxyphenyl)-5-propylthieno[3,2-b]thiophene
2-(p-heptoxyphenyl)-5-propylthieno[3,2-b]thiophene
2-(p-nonoxyphenyl)-5-propylthieno[3,2-b]thiophene
2-(p-decoxyphenyl)-5-propylthieno[3,2-b]thiophene
2-(p-undecoxyphenyl)-5-propylthieno[3,2-b]thiophene
2-(p-dodecoxyphenyl)-5-propylthieno[3,2-b]thiophene
2-(p-ethylphenyl)-5-pentylthieno[3,2-b]thiophene 2-(p-propylphenyl)-5-pentylthieno[3,2-b]thiophene
2-(p-butylphenyl)-5-pentylthieno[3,2-b]thiophene
2-(p-pentylphenyl)-5-pentylthieno[3,2-b]thiophene
2-(p-heptylphenyl)-5-pentylthieno[3,2-b]thiophene
2-(p-cyanophenyl)-5-pentylthieno[3,2-b]thiophene
2-(p-methoxyphenyl)-5-pentylthieno[3,2-b]thiophene
2-(p-ethoxyphenyl)-5-pentylthieno[3,2-b]thiophene
2-(p-butoxyphenyl)-5-pentylthieno[3,2-b]thiophene
2-(p-pentoxyphenyl)-5-pentylthieno[3,2-b]thiophene
2-(p-heptoxyphenyl)-5-pentylthieno[3,2-b]thiophene
2-(p-nonoxyphenyl)-5-pentylthieno[3,2-b]thiophene
2-(p-decoxyphenyl)-5-pentylthieno[3,2-b]thiophene
2-(p-undecoxyphenyl)-5-pentylthieno[3,2-b]thiophene
2-(p-dodecoxyphenyl)-5-penthylthieno[3,2-b]thiophene
2-(p-ethylphenyl)-5-hexylthieno[3,2-b]thiophene
2-(p-propylphenyl)-5-hexylthieno[3,2-b]thiophene
2-(p-butylphenyl)-5-hexylthieno[3,2-b]thiophene
2-(p-pentylphenyl)-5-hexylthieno[3,2-b]thiophene
2-(p-heptylphenyl)-5-hexylthieno[3,2-b]thiophene
2-(p-cyanophenyl)-5-hexylthieno[3,2-b]thiophene
2-(p-methoxyphenyl)-5-hexylthieno[3,2-b]thiophene
2-(p-ethoxyphenyl)-5-hexylthieno[3,2-b]thiophene
2-(p-butoxyphenyl)-5-hexylthieno[3,2-b]thiophene
2-(p-pentoxyphenyl)-5-hexylthieno[3,2-b]thiophene
2-(p-heptoxyphenyl)-5-hexylthieno[3,2-b]thiophene
2-(p-nonoxyphenyl)-5-hexylthieno[3,2-b]thiophene
2-(p-decoxyphenyl)-5-hexylthieno[3,2-b]thiophene
2-(p-undecoxyphenyl)-5-hexylthieno[3,2-b]thiophene
2-(p-dodecoxyphenyl)-5-hexylthieno[3,2-b]thiophene
2-(4'-ethylbiphenyl-4-yl)-5-propylthieno[3,2-b]thiophene
2-(4'-propylbiphenyl-4-yl)-5-propylthieno[3,2-b]thiophene
2-(4'-butylbiphenyl-4-yl)-5-propylthieno[3,2-b]thiophene
2-(4'-pentylbiphenyl-4-yl)-5-propylthieno[3,2-b]thiophene
2-(4'-heptylbiphenyl-4-yl)-5-propylthieno[3,2-b]thiophene
2-(4'-cyanobiphenyl-4-yl)-5-propylthieno[3,2-b]thiophene
2-(4'-methoxybiphenyl-4-yl)-5-propylthieno[3,2-b]thiophene
2-(4'-ethoxybiphenyl-4-yl)-5-propylthieno[3,2-b]thiophene
2(4'-butoxybiphenyl-4-yl)-5-propylthieno[3,2-b]thiophene
2-(4'-pentoxybiphenyl-4-yl)-5-propylthieno[3,2-b]thiophene
2-(4'-heptoxybiphenyl-4-yl)-5-propylthieno[3,2-b]thiophene
2-(4'-nonoxybiphenyl-4-yl)-5-propylthieno[3,2-b]thiophene
2-(4'-decoxybiphenyl-4-yl)-5-propylthieno[3,2-b]thiophene
2-(4'-undecoxybiphenyl-4-yl)-5-propylthieno[3,2-b]thiophene
2-(4'-dodecoxybiphenyl-4-yl)-5-propylthieno[3,2-b]thiophene
2-(4'-ethylbiphenyl-4-yl)-5-pentylthieno[3,2-b]thiophene
2-(4'-propylbiphenyl-4-yl)-5-pentylthieno[3,2-b]thiophene
2-(4'-butylbiphenyl-4-yl)-5-pentylthieno[3,2-b]thiophene
2-(4'-pentylbiphenyl-4-yl)-5-pentylthieno[3,2-b]thiophene
2-(4'-heptylbiphenyl-4-yl)-5-pentylthieno[3,2-b]thiophene
2-(4'-cyanobiphenyl-4-yl)-5-pentylthieno[3,2-b]thiophene
2-(4'-methoxybiphenyl-4-yl)-5-pentylthieno[3,2-b]thiophene
2-(4'-ethoxybiphenyl-4-yl)-5-pentylthieno[3,2-b]thiophene
2-(4'-butoxybiphenyl-4-yl)-5-pentylthieno[3,2-b]thiophene
2-(4'-pentoxybiphenyl-4-yl)-5-pentylthieno[3,2-b]thiophene
2-(4'-heptoxybiphenyl-4-yl)-5-pentylthieno[3,2-b]thiophene
2-(4'-nonoxybiphenyl-4-yl)-5-pentylthieno[3,2-b]thiophene
2-(4'-decoxybiphenyl-4-yl)-5-pentylthieno[3,2-b]thiophene
2-(4'-undecoxybiphenyl-4-yl)-5-pentylthieno[3,2-b]thiophene
2-(4'-dodecoxybiphenyl-4-yl)-5-pentylthieno[3,2-b]thiophene

EXAMPLE 7

A mixture of 12 g of 5-n-pentyl-thieno[3,2-b]thiophene-2-carbamidine (obtainable by reacting the nitrile with hydrogen chloride/ethanol and subsequently with ammonia) and 11,4 g of n-pentyl-malonicdialdehyde tetraethylacetal is heated for 12 hours at −160° (bath temperature). The crystals obtained after cooling are purified by chromatography and crystallization. 2-(5-n-pentylthieno[3,2-b]thiophen-2-yl)-5-n-pentyl-primidine is obtained, M.p. 118°, c.p. 106° (monotropic).

The following compounds are prepared analogously:
2-(5-pentylthieno[3,2-b]thiophen-2-yl)-5-propylpyrimidine,
2-(5-pentylthieno[3,2-b]thiophen-2-yl)-5-butylpyrimidine,
2-(5-pentylthieno[3,2-b]thiophen-2-yl)-5-hexylpyrimidine,
2-(5-pentylthieno[3,2-b]thiophen-2-yl)-5-heptylpyrimidine, M.p. 102°, c.p. 106°,
2-(5-pentylthieno[3,2-b]thiophen-2-yl)-5-nonylpyrimidine
2-(5-propylthieno[3,2-b]thiophen-2-yl)-5-ethylpyrimidine
2-(5-propylthieno[3,2-b]thiophen-2-yl)-5-propylpyrimidine
2-(5-propylthieno[3,2-b]thiophen-2-yl)-5-butylpyrimidine
2-(5-propylthieno[3,2-b]thiophen-2-yl)-5-pentylpyrimidine
2-(5-propylthieno[3,2-b]thiophen-2-yl)-5-hexylpyrimidine
2-(5-propylthieno[3,2-b]thiophen-2-yl)-5-heptylpyrimidine
2-(5-heptylthieno[3,2-b]thiophen-2-yl)-5-ethylpyrimidine
2-(5-heptylthieno[3,2-b]thiophen-2-yl)-5-propylpyrimidine
2-(5-heptylthieno[3,2-b]thiophen-2-yl)-5-butylpyrimidine
2-(5-heptylthieno[3,2-b]thiophen-2-yl)-5-pentylpyrimidine
2-(5-heptylthieno[3,2-b]thiophen-2-yl)-5-hexylpyrimidine 2-(5-heptylthieno[3,2-b]thiophen-2-yl)-5-heptylpyrimidine
2-(5-cyanothieno[3,2-b]thiophen-2-yl)-5-ethylpyrimidine
2-(5-cyanothieno[3,2-b]thiophen-2-yl)-5-propylpyrimidine
2-(5-cyanothieno[3,2-b]thiophen-2-yl)-5-butylpyrimidine
2-(5-cyanothieno[3,2-b]thiophen-2-yl)-5-pentylpyrimidine
2-(5-cyanothieno[3,2-b]thiophen-2-yl)-5-hexylpyrimidine
2-(5-cyanothieno[3,2-b]thiophen-2-yl)-5-heptylpyrimidine
2-(5-methoxythieno[3,2-b]thiophen-2-yl)-5-ethylpyrimidine
2-(5-methoxythieno[3,2-b]thiophen-2-yl)-5-propylpyrimidine
2-(5-methoxythieno[3,2-b]thiophen-2-yl)-5-butylpyrimidine
2-(5-methoxythieno[3,2-b]thiophen-2-yl)-5-pentylpyrimidine
2-(5-methoxythieno[3,2-b]thiophen-2-yl)-5-hexylpyrimidine
2-(5-methoxythieno[3,2-b]thiophen-2-yl)-5-heptylpyrimidine
2-(5-ethoxythieno[3,2-b]thiophen-2-yl)-5-ethylpyrimidine
2-(5-ethoxythieno[3,2-b]thiophen-2-yl)-5-propylpyrimidine
2-(5-ethoxythieno[3,2-b]thiophen-2-yl)-5-butylpyrimidine
2-(5-ethoxythieno[3,2-b]thiophen-2-yl)-5-pentylpyrimidine
2-(5-ethoxythieno[3,2-b]thiophen-2-yl)-5-hexylpyrimidine
2-(5-ethoxythieno[3,2-b]thiophen-2-yl)-5-heptylpyrimidine
2-(5-butoxythieno[3,2-b]thiophen-2-yl)-5-ethylpyrimidine
2-(5-butoxythieno[3,2-b]thiophen-2-yl)-5-propylpyrimidine
2-(5-butoxythieno[3,2-b]thiophen-2-yl)-5-butylpyrimidine
2-(5-butoxythieno[3,2-b]thiophen-2-yl)-5-pentylpyrimidine
2-(5-butoxythieno[3,2-b]thiophen-2-yl)-5-hexylpyrimidine
2-(5-butoxythieno[3,2-b]thiophen-2-yl)-5-heptylpyrimidine
2-(5-hexoxythieno[3,2-b]thiophen-2-yl)-5-ethylpyrimidine
2-(5-hexoxythieno[3,2-b]thiophen-2-yl)-5-propylpyrimidine
2-(5-hexoxythieno[3,2-b]thiophen-2-yl)-5-butylpyrimidine
2-(5-hexoxythieno[3,2-b]thiophen-2-yl)-5-pentylpyrimidine
2-(5-hexoxythieno[3,2-b]thiophen-2-yl)-5-hexylpyrimidine
2-(5-hexoxythieno[3,2-b]thiophen-2-yl)-5-heptylpyrimidine
2-(5-octoxythieno[3,2-b]thiophen-2-yl)-5-ethylpyrimidine
2-(5-octoxythieno[3,2-b]thiophen-2-yl)-5-propylpyrimidine
2-(5-octoxythieno[3,2-b]thiophen-2-yl)-5-butylpyrimidine
2-(5-octoxythieno[3,2-b]thiophen-2-yl)-5-pentylpyrimidine
2-(5-octoxythieno[3,2-b]thiophen-2-yl)-5-hexylpyrimidine
2-(5-octoxythieno[3,2-b]thiophen-2-yl)-5-heptylpyrimidine
2-(5-nonoxythieno[3,2-b]thiophen-2-yl)-5-ethylpyrimidine
2-(5-nonoxythieno[3,2-b]thiophen-2-yl)-5-propylpyrimidine
2-(5-nonoxythieno[3,2-b]thiophen-2-yl)-5-butylpyrimidine
2-(5-nonoxythieno[3,2-b]thiophen-2-yl)-5-pentylpyrimidine
2-(5-nonoxythieno[3,2-b]thiophen-2-yl)-5-hexylpyrimidine
2-(5-nonoxythieno[3,2-b]thiophen-2-yl)-5-heptylpyrimidine
2-(5-decoxythieno[3,2-b]thiophen-2-yl)-5-ethylpyrimidine
2-(5-decoxythieno[3,2-b]thiophen-2-yl)-5-propylpyrimidine
2-(5-decoxythieno[3,2-b]thiophen-2-yl)-5-butylpyrimidine
2-(5-decoxythieno[3,2-b]thiophen-2-yl)-5-pentylpyrimidine
2-(5-decoxythieno[3,2-b]thiophen-2-yl)-5-hexylpyrimidine
2-(5-decoxythieno[3,2-b]thiophen-2-yl)-5-heptylpyrimidine
2-(5-undecoxythieno[3,2-b]thiophen-2-yl)-5-ethylpyrimidine
2-(5-undecoxythieno[3,2-b]thiophen-2-yl)-5-propylpyrimidine
2-(5-undecoxythieno[3,2-b]thiophen-2-yl)-5-butylpyrimidine
2-(5-undecoxythieno[3,2-b]thiophen-2-yl)-5-pentylpyrimidine
2-(5-undecoxythieno[3,2-b]thiophen-2-yl)-5-hexylpyrimidine
2-(5-undecoxythieno[3,2-b]thiophen-2-yl)-5-heptylpyrimidine
2-(5-dodecoxythieno[3,2-b]thiophen-2-yl)-5-ethylpyrimidine
2-(5-dodecoxythieno[3,2-b]thiophen-2-yl)-5-propylpyrimidine
2-(5-dodecoxythieno[3,2-b]thiophen-2-yl)-5-butylpyrimidine
2-(5-dodecoxythieno[3,2-b]thiophen-2-yl)-5-pentylpyrimidine
2-(5-dodecoxythieno[3,2-b]thiophen-2-yl)-5-hexylpyrimidine
2-(5-dodecoxythieno[3,2-b]thiophen-2-yl)-5-heptylpyrimidine

EXAMPLE 8

A mixture of 3,5 g of 5-n-pentylthieno[2,3-b]thiophene-2-carboxylic acid chloride [obtainable by reacting 5-n-pentyl-thieno(2,3-b)thiophene-2-carboxylic acid (m.p. 188°, c.p. 187° (monotropic)] with thionyl chloride; the acid is obtainable by reacting ethyl ester of (5-n-pentyl-3-formyl-2-thienylmercapto)acetic acid [obtainable by reacting 2-n-pentylthiophene with butyllithium, sulfur and ethyl ester of chloroacetic acid and followed by Vilsmeyer formylation of the obtained 5-n-pentyl-2-thienylmercapto-acetic ester] with sodium ethylate[ethanol] in 20 ml of toluene was added dropwise to a mixture of 2,25 g of 4-n-pentylphenol, 1,08 g of pyridine and 30 ml of toluene, the mixture is heated to the boil for 2 hours and allowed to cool, the pyridine hydrochloride is filtered off, and the mixture is worked up in the usual manner.

4-n-Pentylphenyl-5-n-pentyl-thieno[2,3-b]thiophene-2-carboxylate of m.p. 51,9° C. and c.p. 90,5° C. is obtained.

The following compounds are prepared analogously:

4-ethylphenyl 5-pentyl-thieno[2,3-b]thiophene-2-carboxylate,
4-propylphenyl 5-pentyl-thieno[2,3-b]thiophene-2-carboxylate,
4-butylphenyl 5-pentyl-thieno[2,3-b]thiophene-2-carboxylate,
4-heptylphenyl 5-pentyl-thieno[2,3-b]thiophene-2-carboxylate,
4-ethylphenyl 5-propyl-thieno[2,3-b]thiophene-2-carboxylate,
4-propylphenyl 5-propyl-thieno[2,3-b]thiophene-2-carboxylate,
4-butylphenyl 5-propyl-thieno[2,3-b]thiophene-2-carboxylate,
4-pentylphenyl 5-propyl-thieno[2,3-b]thiophene-2-carboxylate,
4-heptylphenyl 5-propyl-thieno[2,3-b]thiophene-2-carboxylate,
4-ethylphenyl 5-butyl-thieno[2,3-b]thiophene-2-carboxylate,
4-propylphenyl 5-butyl-thieno[2,3-b]thiophene-2-carboxylate,
4-butylphenyl 5-butyl-thieno[2,3-b]thiophene-2-carboxylate,
4-pentylphenyl 5-butyl-thieno[2,3-b]thiophene-2-carboxylate,
4-heptylphenyl-5-butyl-thieno[2,3-b]thiophene-2-carboxylate,
4-ethylphenyl 5-heptyl-thieno[2,3-b]thiophene-2-carboxylate,
4-propylphenyl 5-heptyl-thieno[2,3-b]thiophene-2-carboxylate,
4-butylphenyl 5-heptyl-thieno[2,3-b]thiophene-2-carboxylate,
4-pentylphenyl 5-heptyl-thieno[2,3-b]thiophene-2-carboxylate,
4-heptylphenyl 5-heptyl-thieno[2,3-b]thiophene-2-carboxylate,
4-ethylphenyl 5-nonyl-thieno[2,3-b]thiophene-2-carboxylate,
4-propylphenyl 5-nonyl-thieno[2,3-b]thiophene-2-carboxylate,
4-butylphenyl 5-nonyl-thieno[2,3-b]thiophene-2-carboxylate,
4-pentylphenyl 5-nonyl-thieno[2,3-b]thiophene-2-carboxylate,
4-heptylphenyl 5-nonyl-thieno[2,3-b]thiophene-2-carboxylate,
4-cyanophenyl 5-propyl-thieno[2,3-b]thiophene-2-carboxylate,
4-cyanophenyl 5-butyl-thieno[2,3-b]thiophene-2-carboxylate,
4-cyanophenyl 5-pentyl-thieno[2,3-b]thiophene-2-carboxylate, m.p. 85°, c.p. 129,2°,
4-cyanophenyl 5-hexyl-thieno[2,3-b]thiophene-2-carboxylate,
4-cyanophenyl 5-heptyl-thieno[2,3-b]thiophene-2-carboxylate,
4-cyanophenyl 5-nonyl-thieno[2,3-b]thiophene-2-carboxylate,
4-fluorophenyl 5-pentyl-thieno[2,3-b]thiophene-2-carboxylate,
4-chlorophenyl 5-pentyl-thieno[2,3-b]thiophene-2-carboxylate,
4-bromophenyl 5-pentyl-thieno[2,3-b]thiophene-2-carboxylate,
4-methoxyphenyl 5-pentyl-thieno[2,3-b]thiophene-2-carboxylate,
4-ethoxyphenyl 5-pentyl-thieno[2,3-b]thiophene-2-carboxylate,
4-propoxyphenyl 5-pentyl-thieno[2,3-b]thiophene-2-carboxylate,
4-butoxyphenyl 5-pentyl-thieno[2,3-b]thiophene-2-carboxylate,
4-pentyloxyphenyl 5-pentyl-thieno[2,3-]thiophene-2-carboxylate,
4-heptyloxyphenyl 5-pentyl-thieno[2,3-b]thiophene-2-carboxylate,
4-nonyloxyphenyl 5-pentyl-thieno[2,3-b]thiophene-2-carboxylate,
4'-propylbiphenylyl 5-pentyl-thieno[2,3-b]thiophene-2-carboxylate,
4'-cyanobiphenylyl 5-pentyl-thieno[2,3-b]thiophene-2-carboxylate,
2'-fluoro-4'-ethylbiphenylyl 5-pentyl-thieno[2,3-b]thiophene-2-carboxylate,
2-methyl-4'-propylbiphenylyl 5-pentyl-thieno[2,3-b]thiophene-2-carboxylate,
4-(4-propylcyclohexyl)-phenyl 5-pentyl-thieno[2,3-b]thiophene-2-carboxylate,
4-(1-cyano-4-propylcyclohexyl)-phenyl 5-pentyl-thieno[2,3-b]thiophene-2-carboxylate and
4-(5-propyl-1,3-dioxan-2-yl)-phenyl 5-pentyl-thieno[2,3-b]thiophene-2-carboxylate.
trans-4-ethylcyclohexyl 5-pentyl-thieno[2,3-b]thiophene-2-carboxylate,
trans-4-propylcyclohexyl 5-pentyl-thieno[2,3-b]thiophene-2-carboxylate, M.p. 60°, c.p. 91°
trans-4-butylcyclohexyl 5-pentyl-thieno[2,3-b]thiophene-2-carboxylate,
trans-4-pentylcyclohexyl 5-pentyl-thieno[2,3-b]thiophene-2-carboxylate,
trans-4-heptylcyclohexyl 5-pentyl-thieno[2,3-b]-thiophene-2-carboxylate,
trans-4-ethylcyclohexyl 5-propyl-thieno[2,3-b]thiophene-2-carboxylate,
trans-4-propylcyclohexyl 5-propyl-thieno[2,3-b]thiophene-2-carboxylate,
trans-4-butylcyclohexyl 5-propyl-thieno[2,3-b]thiophene-2-carboxylate,
trans-4-pentylcyclohexyl 5-propyl-thieno[2,3-b]thiophene-2-carboxylate,
trans-4-heptylcyclohexyl 5-propyl-thieno[2,3-b]thiophene-2-carboxylate,
trans-4-ethoxycyclohexyl 5-propyl-thieno[2,3-b]thiophene-2-carboxylate,
trans-4-butoxycyclohexyl 5-propyl-thieno[2,3-b]thiophene-2-carboxylate,
trans,trans-4-ethylbicyclohex-4'-yl 5-propyl-thieno[2,3-b]thiophene-2-carboxylate
trans,trans-4-propylbicyclohex-4'-yl 5-propyl-thieno[2,3-b]thiophene-2-carboxylate
trans,trans-4-butylbicyclohex-4'-yl 5-propyl-thieno[2,3-b]thiophene-2-carboxylate
trans,trans-4-pentylbicyclohex-4'-yl 5-propyl-thieno[2,3-b]thiophene-2-carboxylate
trans,trans-4-heptylbicyclohex-4'-yl 5-propyl-thieno[2,3-b]thiophene-2-carboxylate trans,trans-4-ethoxybicyclohex-4'-yl 5-propyl-thieno[2,3-b]thiophene-2-carboxylate trans,trans-4-butoxybicyclohex-4'-yl 5-propyl-thieno[2,3-b]thiophene-2-carboxylate trans,trans-4-propionyloxybicyclohex-4'-yl 5-propyl-thieno[2,3-b]thiophene-2-carboxylate Examples of liquid crystalline phases according to the invention which contain at least one compound of the formula I are given below:

EXAMPLE A

A liquid crystalline phase consisting of
15% of p-trans-4-ethylcyclohexylbenzonitrile,
15% of p-trans-4-butylcyclohexylbenzonitrile,
10% of 4-ethyl-4'-cyanobiphenyl,
13% of 4-butyl-4'-cyanobiphenyl,
11% of 4-cyano-4'-(trans-4-pentylcyclohexyl)-biphenyl,
6% of 4-p-cyanophenyl-4'-pentylbiphenyl,
15% of 4-pentylphenyl 5-pentylthieno[3,2-b]thiophene-2-carboxylate and
15% of 4-propylphenyl 5-propylthieno[3,2-b]thiophene-2-carboxylate
has a melting point of −8°, a clear point of 67° and a viscosity of 29 cSt.

EXAMPLE B

A liquid crystalline phase consisting of
8% of 2-p-cyanophenyl-5-ethyl-1,3-dioxane,
9% of 2-p-cyanophenyl-5-propyl-1,3-dioxane,
4% of p-cyanophenyl p-ethylbenzoate,
3% of p-cyanophenyl p-propylbenzoate,
11% of p-trans-4-ethylcyclohexylbenzonitrile,
13% of p-trans-4-butylcyclohexylbenzonitrile,
8% of 4-ethyl-4'-cyanobiphenyl,
12% of 4-butyl-4'-cyanobiphenyl,
5% of p-cyanophenyl p-trans-4-pentylcyclohexylbenzoate,
9% of 4-cyanophenyl 5-propylthieno[3,2-b]thiophene-2-carboxylate,
9% of 4-cyanophenyl 5-pentylthieno[3,2-b]thiophene-2-carboxylate and
9% of 4-cyanophenyl 5-heptylthieno[3,2-b]thiophene-2-carboxylate
has a melting point of −11°, a clear point of 61° and a viscosity of 36 cSt. An electro-optical display element containing this phase as a dielectric has a low threshold voltage V₁₀ of 1.15 V.

EXAMPLE C

A liquid crystalline phase consisting of
10% of 2-p-cyanophenyl-5-ethyl-1,3-dioxane,
10% of 2-p-cyanophenyl-5-propyl-1,3-dioxane,
16% of 2-p-cyanophenyl-5-butyl-1,3-dioxane,
10% of 2-p-cyanophenyl-5-pentyl-1,3-dioxane,
18% of 4-propylphenyl 5-propylthieno[3,2-b]thiophene-2-carboxylate,
18% of 4-pentylphenyl 5-pentylthieno[3,2-b]thiophene-2-carboxylate and
18% of 4-heptylphenyl 5-pentylthieno[3,2-b]thiophene-2-carboxylate
has a melting point of −10°, a clear point of 62° and a viscosity of 31 cSt.

EXAMPLE D

A liquid crystalline phase consisting of
4% of 2-p-cyanophenyl-5-propyl-1,3-dioxane,
5% of 2-p-cyanophenyl-5-butyl-1,3-dioxane,
4% of 2-p-cyanophenyl-5-pentyl-1,3-dioxane,
10% of p-methoxyphenyl trans-4-propylcyclohexanecarboxylate,
11% of p-ethoxyphenyl trans-4-propylcyclohexanecarboxylate,
15% of p-methoxyphenyl trans-4-butylcyclohexanecarboxylate,
10% of p-ethoxyphenyl trans-4-butylcyclohexanecarboxylate,
10% of p-methoxyphenyl trans-4-pentylcyclohexanecarboxylate,
13% of p-pentylphenyl trans-4-pentylcyclohexanecarboxylate,
6% of 4-cyanophenyl 5-propylthieno[3,2-b]thiophene-2-carboxylate,
7% of 4-cyanophenyl 5-pentylthieno[3,2-]thiophene-2-carboxylate and
5% of 4-cyanophenyl 5-heptylthieno[3,2-b]thiophene-2-carboxylate
has a melting point of −12°, a clear point of 71° and a viscosity of 18 cSt. In an electro-optical display element, this dielectric has good multiplex properties (1:32).

EXAMPLE E

A liquid crystalline phase consisting of
18.0% of p-trans-4-propylcyclohexylbenzonitrile,
13.5% of p-trans-4-butylcyclohexylbenonitrile,
24.5% of p-trans-4-pentylcyclohexylbenonitrile,
15.5% of p-trans-4-heptylcyclohexylbenonitrile,
7.0% of 4-cyano-4'-(trans-4-pentylcyclohexyl)-biphenyl,
7.0% of 4-(trans-4-pentylcyclohexyl)-4'-(trans-4-propylcyclohexyl)-biphenyl,
6.0% of 4-p-cyanophenyl-4'-pentyl-biphenyl,
8.0% of p-trans-propylcyclohexylphenyl trans-4-butylcyclohexanecarboxylate and
0.5% of 4-cyanophenyl 5-pentylthieno[3,2-b]thiophene-2-carboxylate
has a melting point of −14° and a clear point of 88°.

EXAMPLE F

A liquid crystalline phase consisting of
14% of p-trans-4-propylcyclohexylbenzonitrile,
16% of 2-p-cyanophenyl-5-butyl-1,3-dioxane,
10% of 2-p-cyanophenyl-5-pentyl-1,3-dioxane,
14% of 4-cyanophenyl 5-propylthieno[3,2-b]thiophene-2-carboxylate,
10% of 4-cyanophenyl 5-pentylthieno[3,2-b]thiophene-2-carboxylate,
8% of 4-cyanophenyl 5-heptylthieno[3,2-b]thiophene-2-carboxylate,
16% of 4-propylphenyl 5-propylthieno[3,2-b]thiophene-2-carboxylate and
12% of 4-pentylphenyl 5-pentylthieno[3,2-b]thiophene-2-carboxylate
is a good host material for pleochroic dyes.

EXAMPLE G

A liquid crystalline phase consisting of
66.6% of p-pentylphenyl p-methoxybenzoate,
33.3% of p-pentylphenyl p-hexyloxybenzoate and
0.1% of 4-propylphenyl 5-propylthieno[3,2-b]thiophene-2-carboxylate
has a melting point of 13°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystalline phase comprising at least two liquid-crystal components, wherein at least one component is of the formula $$R^1-(A^1)_m-Z^1-A-(Z^2-A^2)_n-R^2$$

wherein
$R^1$ and $R^2$ are independently each H, alkyl of 1-12 C-atoms, or alkyl of 1-12 C-atoms, in which one or two non-adjacent CH$_2$ groups are replaced by an oxa atom, —CO— or —CH=CH—, in each case the resultant groups having 1-12 C— and oxa atoms in total, or independently are each F, Cl, Br, CN, —COOR or —O—COR;
$A^1$ and $A^2$ are independently each 1,4-phenylene, 1,4-cyclohexylene, 1,3-dioxane-2,5-diyl, 1,3-dithiane-2,5-diyl, tetrahydropyran-2,5-diyl, pyridazine-3,6-diyl or the corresponding N-oxide, piperidine-1,4-diyl, 1,4-bicyclo[2.2.2]octylene or pyrimidine-2,5-diyl each of which is unsubstituted or substituted by one or two of F, Cl, Br, CN or CH$_3$;
A is a group of the formula 1 or 2

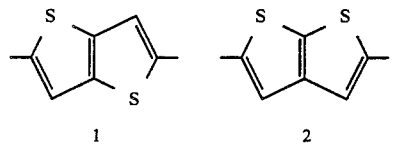

each of which is unsubstituted or substituted by one or two Cl or Br atoms;
$Z^1$ and $Z^2$ are independently each —CO—O—, —O—CO—, —CH$_2$CH$_2$—, —OCH$_2$—, —CH$_2$O— or a single bond;
R is alkyl of 1-10 C-atoms;
m is 1 or 2;
n is 0 or 1; and
when m is 2, the two groups $A^1$ are identical or different.

2. A liquid crystalline phase of claim 1 wherein at least one compound is of the formula $$R^1-A^1-Z^1-A-R^2.$$

3. A liquid crystalline phase of claim 1 wherein at least one compound is of the formula $$R^1-A^1-Z^1-A-Z^2-A^2-R^2.$$

4. A liquid crystalline phase of claim 1 wherein at least one compound is of the formula $$R^1-(A^1)_2-Z^1-A-R^2.$$

5. A liquid crystalline phase of claim 1 wherein at least one compound is of the formula $$R^1-(A^1)_2-Z^1-A-Z^2-A^2-R^2.$$

6. A liquid crystalline phase of claim 2 wherein at least one compound is of the formula $$R^1-Phe-Z^1-A-R^2$$

$$R^1-Cy-Z^1-A-R^2$$

$$R^1-Dio-Z^1-A-R^2$$

$$R^1-Pip-Z^1-A-R^2$$

$$R^1-Bic-Z^1-A-R^2 \text{ or}$$

$$R^1-Pyr-Z^1-A-R^2$$

wherein Phe is 1,4-phenylene, Cy is 1,4-cyclohexylene, Dio is 1,3-dioxane-2,5-diyl, Bi is bicyclo[2.2.2.]octylene, Pip is piperidine-1,4-diyl and Pyr is pyrimidine-2,5-diyl.

7. A liquid crystalline phase of claim 6 wherein at least one compound is of the formula $$R^1-Phe-Z^1-A-R^2$$

$$R^1-Cy-Z^1-A-R^2 \text{ or}$$

$$R^1-Dio-Z^1-A-R^2$$

8. A liquid crystalline phase of claim 1 wherein at least one compound is of the formula $$R^1-Phe-Z^1-A-Z^2-Phe-R^2$$

$$R^1-Dio-Z^1-A-Z^2-Cy-R^2$$

$$R^1-Cy-Z^1-A-Z^2-Phe-R^2$$

$$R^1-Cy-Z^1-A-Z^2-Cy-R^2$$

$$R^1-Phe-Phe-Z^1-A-R^2$$

$$R^1-Phe-Cy-Z^1-A-R^2$$

$$R^1-Cy-Phe-Z^1-A-R^2$$

$$R^1-Cy-Cy-Z^1-A-R^2$$

$$R^1-Phe-Phe-Z^1-A-Z^2-Phe-R^2$$

$$R^1-Phe-Phe-Z^1-A-Z^2-Cy-R^2$$

$$R^1-Phe-Cy-Z^1-A-Z^2-Phe-R^2$$

$$R^1-Phe-Cy-Z^1-A-Z^2-Cy-R^2$$

$$R^1-Cy-Phe-Z^1-A-Z^2-Phe-R^2$$

$$R^1-Cy-Phe-Z^1-A-Z^2-Cy-R^2$$

$$R^1-Cy-Cy-Z^1-A-Z^2-Phe-R^2 \text{ or}$$

$$R^1-Cy-Cy-Z^1-A-Z^2-Cy-R^2$$

wherein Phe is 1,4-phenylene, Cy is 1,4-cyclohexylene and Dio is a 1,3-dioxane-2,5-diyl group.

9. A liquid crystalline phase of claim 1 wherein at least one compound is of the formula $$R^1-Phe-A-R^2$$

$$R^1-Phe-CO-O-A-R^2$$

$$R^1-Phe-O-CO-A-R^2$$

$$R^1-Phe-CH_2CH_2-A-R^2$$

$$R^1-Phe-O-CH_2-A-R^2$$

$$R^1-Phe-CH_2-O-A-R^2$$

$$R^1-Cy-A-R^2$$

R¹—Cy—O—CO—A—R²

R¹—Cy—CH₂CH₂—A—R²

R¹—Cy—O—CH₂—A—R²

R¹—Cy—CH₂—O—A—R²

R¹—Dio—A—R²

R¹—Pip—A—R²

R¹—Bic—A—R²

R¹—Pyr—A—R² or

R¹—Phe—Phe—A—R² wherein Phe is 1,4-phenylene, Cy is 1,4-cyclohexylene, Dio is 1,3-dioxane-2,5-diyl, Bi is bicyclo[2.2.2.]octylene, Pip is piperidine-1,4-diyl and Pyr is pyrimidine-2,5-diyl.

10. A liquid crystalline phase of claim 1 wherein R1 and R2 are each alkyl or oxaalkyl.

11. A liquid crystalline phase of claim 1 wherein A¹ and A² are b 1,4-cyclohexylene, 1,4-phenylene, or pyrimidine-2,5-diyl.

12. A liquid crystalline phase of claim 1 wherein one of Z¹ and Z² is a single bond and the other is —O—CO—, —CO—O— or —CH₂CH₂—.

13. In a liquid crystalline phase comprising at least two liquid-crystal components, wherein at least one is a compound having the structure
ti wing group-ring-(bridging element-ring)₍₁₋₃₎-wing group wherein the ring groups, the bridging elements and at least one ring are conventional structural elements in liquid crystal compounds, the improvement wherein one ring is of the formula

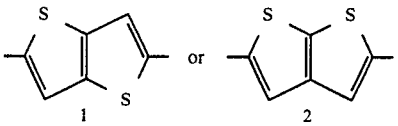

and said at least one compound is present in an amount effective to improve the elastic properties of the phase.

14. In a liquid crystal display element comprising a liquid crystalline phase, the improvement wherein the phase is one of claim 1.

15. In an electro-optical display element, comprising a liquid crystalline dielectric, the improvement wherein the latter is a liquid crystalline phase of claim 1.

16. In an electro-optical display element, comprising a liquid crystalline dielectric, the improvement wherein the latter is a liquid crystalline phase of claim 13.

17. A liquid crystalline phase of claim 1, wherein R¹ and R² are independently each alkyl of 1-12 C-atoms, or alkyl of 1-12 C-atoms, in which one or two non-adjacent CH₂ groups are replaced by an oxa atom, —CO— or —CH=CH—, in each case the resultant groups having 1-12 C— and oxa atoms in total, or independently are each F, Cl, Br, CN, —COOR or —O—COR.

18. A liquid crystalline phase of claim 1, wherein A¹ and A² are each independently 1,4-phenylene or 1,4-cyclohexylene, each unsubstituted or substituted by one F or CN group; Z¹ is —CO—O—, —O—CO—, —CH₂CH₂— or a single bond; and Z² is a single bond.

* * * * *